United States Patent
Sasaki

[11] Patent Number: 6,090,856
[45] Date of Patent: Jul. 18, 2000

[54] REMEDIES FOR FREQUENT URINATION AND URINARY INCONTINENCE

[75] Inventor: Yasuo Sasaki, Kameoka, Japan

[73] Assignee: Nippon Shinyaku Co., Ltd., Kyoto, Japan

[21] Appl. No.: 09/402,942

[22] PCT Filed: Apr. 8, 1998

[86] PCT No.: PCT/JP98/01633
 § 371 Date: Jan. 3, 2000
 § 102(e) Date: Jan. 3, 2000

[87] PCT Pub. No.: WO98/46216
 PCT Pub. Date: Oct. 22, 1998

[30] Foreign Application Priority Data

Apr. 11, 1997 [JP] Japan .................................. 9-093809

[51] Int. Cl.⁷ .................................................. A61K 31/135
[52] U.S. Cl. .............................................................. 514/646
[58] Field of Search ................................................ 514/646

[56] References Cited

FOREIGN PATENT DOCUMENTS

WO 93/04675 3/1993 WIPO .
WO 93/15062 8/1993 WIPO .

OTHER PUBLICATIONS

The Department of Biochemical Pharmacology and Pharmacology, Grunethal GmbH, Aachen (Fed. Rep. of Germany) entitled Receptor Binding, Analgesic and Antitussive Potency of Tramadol and Other Selected Opioids ( Publication date not available).

*Primary Examiner*—Raymond Henley, III
*Attorney, Agent, or Firm*—Graham & James LLP

[57] ABSTRACT

The object of this invention is to provide a novel medicinal use for tramadol the safety, among other properties, of which has already been established. This invention is directed to a therapeutic or prophylactic composition for urinary frequency and a therapeutic or prophylactic composition for urinary incontinence, both comprising tramadol or a salt thereof. The preferable salt of tramadol includes tramadol hydrochloride.

4 Claims, No Drawings

REMEDIES FOR FREQUENT URINATION AND URINARY INCONTINENCE

TECHNICAL FIELD

This invention relates to a therapeutic or prophylactic composition for urinary frequency or a therapeutic or prophylactic composition for urinary incontinence, which comprises tramadol or a salt thereof as an active ingredient.

BACKGROUND ART

Tramadol is an opioid non-narcotic analgesic drug having the chemical name of trans-(±)-2-[(dimethylamino)methyl]-1-(3-methoxyphenyl)cyclohexanol and has heretofore been used broadly in the form of hydrochloride for the management of intense to moderate pain.

Urinary incontinence is a disease generally considered to occur when the intravesical pressure involuntarily exceeds the urethral closure pressure and is suspected to involve, as an etiologic factor, an increase in intravesical pressure (which chiefly causes urge urinary incontinence or urinary frequency) or a decrease in urethral closure pressure (which chiefly causes stress urinary incontinence).

The current pharmacotherapeutic regimen in urinary frequency or urinary incontinence includes the drugs adapted to lower intravesical pressure, i.e. decrease the contractility of the detrusor muscle, such as anticholinergic drugs (e.g. oxybutynin, propiverine), tricyclic antidepressants (e.g. imipramine), smooth muscle direct relaxants (e.g. flavoxate), etc., and the drugs adapted to increase the urethral closure pressure, i.e. increase the resistance of bladder neck or the urethra, such as α-adrenergic agonists (e.g. ephedrine), β-adrenergic agonists (e.g. clenbuterol) and female hormones (e.g. estradiol). Opioid analgesics are not included in this therapeutic regimen.

Up to the present, there is no report indicating that any drug belonging to the established and clinically accepted class of opioid analgesics, represented by morphine, is ever effective in the treatment of urinary frequency or urinary incontinence. In addition, as to tramadol, it is not known at all that, as a main efficacy, this drug is effective in the therapy of urinary frequency or urinary incontinence.

DISCLOSURE OF INVENTION

The object of this invention is to provide a novel medicinal use for tramadol the safety, among other properties, of which has already been established.

The inventors of this invention did intensive investigations and found that tramadol is effective in the treatment of urinary frequency or urinary incontinence as a main efficacy. This invention has come forth from the above finding.

This invention is directed to a therapeutic or prophylactic composition for urinary frequency and a therapeutic or prophylactic composition for urinary incontinence, both comprising tramadol or a salt thereof [hereinafter referred to as the drug of the invention] as an active ingredient [both compositions are collectively referred to herein as the pharmaceutical composition of this invention]. This invention may be defined also as the use of the drug of the invention for the manufacture of said pharmaceutical composition for the therapy or prophylaxis of urinary frequency or said pharmaceutical composition for the therapy or prophylaxis of urinary incontinence, which contain the drug of the invention as an active ingredient. Furthermore, this invention may also be defined as a method for the therapy or prophylaxis of urinary frequency or urinary incontinence which comprises using the drug of the invention.

The salt of tramadol is not particularly restricted as far as it is a pharmaceutically acceptable acid addition salt, thus including salts with inorganic acid, e.g. hydrochloride, sulfate, nitrate, phosphate, hydrofluoride, hydrobromide, etc. and salts with organic acids such as acetate, tartrate, lactate, citrate, fumarate, maleate, succinate, methanesulfonate, benzenesulfonate, toluenesulfonate, naphthalenesulfonate, camphorsulfonate and so forth. Particularly preferred is tramadol hydrochloride which is in broad use as an analgesic.

BEST MODE FOR CARRYING OUT THE INVENTION

The pharmaceutical composition of the invention or the drug of the invention can be used in the therapy or prophylaxis of urinary frequency or urinary incontinence (mainly urge urinary incontinence and stress urinary incontinence) in animals inclusive of humans.

The dosage of the drug of the invention varies with the patient's age, body weight and other background, the route of administration, the nature and stage of disease, among other factors, but the usual daily dosage for an adult human may judiciously fall within the range of 0.01–400 mg, preferably 0.1–200 mg, more preferably 1–100 mg. Reduced doses may be sufficient in some cases, while some escalation of said dosage may be needed in other cases. The drug of the invention can be used in a dose range not over the usual dose range for use as an analgesic. Moreover, the pharmaceutical composition (drug) of the invention may be administered in 2–5 divided doses a day.

The pharmaceutical composition of the invention may comprise the drug of the invention as it is or contain the same as formulated, within a range of 0.01%–99.5%, more preferably 0.5%–90%, in a pharmaceutically acceptable, nontoxic and inert carrier.

As the carrier mentioned above, one or more of solid, semisolid or liquid diluents, fillers and/or other auxiliary formulating additives can be used. The pharmaceutical composition of the invention is preferably administered in unit dosage forms. Thus, the pharmaceutical composition of the invention may be provided in any of oral dosage forms, e.g. bulk powder, capsules, tablets, sugar-coated tablets, granules, powders, suspension, solution, syrup, elixir, drops, sublingual tablets, etc., and non-oral dosage forms, e.g. injections, suppositories, etc., regardless of whether it is in a solid form or in a liquid form but each containing a unit dose. It may also be a sustained-release dosage form. Particularly preferred is an oral dosage form, such as tablets.

The bulk powder can be prepared by comminuting the drug of the invention to a suitable particle size. The powder can be manufactured by comminuting the drug of the invention to a suitable particle size and blending it with a similarly comminuted pharmaceutical carrier such as an edible carbohydrate, e.g. starch and mannitol, or the like. Optionally, a corrigent, a preservative, a dispersant, a coloring agent, a flavoring agent and/or other additives may also be formulated.

The capsules can be manufactured by filling the bulk powder or powder prepared by said comminuting technology or the granules prepared by the method to be described below for tablets into capsule shells, e.g. gelatin capsule shells. Preceding this filling operation, the above powdery or granular preparation may be supplemented and blended with a lubricant or fluidizing agent such as colloidal silica, talc, magnesium stearate, calcium stearate and solid polyethylene glycol. The efficacy of the drug after intake of the capsules is enhanced by addition of a disintegrator or solubilizing agent such as carboxymethyl-cellulose, carboxymethylcellulose calcium, low-substitution-degree hydroxypropylcellulose, croscarmellose sodium, carboxymethylstarch sodium, calcium carbonate and sodium carbonate. Furthermore, a finely divided powder of the drug of the invention may be suspended and dispersed in vegetable oil, polyethylene glycol, glycerin or a surfactant and the dispersion be packaged with gelatin sheet to provide soft capsules.

The tablets can be manufactured by adding an excipient, granulating or slugging the resulting mixed powder, adding a disintegrator or a lubricant and compressing the mixture. The mixed powder can be prepared by blending a suitably comminuted powder of the drug with said diluent or a base, optionally with the addition of a binder (e.g. carboxymethylcellulose sodium, methylcellulose, hydroxypropylmethylcellulose, gelatin, polyvinylpyrrolidone, polyvinyl alcohol, etc.), a dissolution retardant (e.g. paraffin), a reabsorption agent (e.g. quaternary salts) and an adsorbent (e.g. bentonite, kaolin, etc.). The mixed powder can be first wetted with a binder such as a syrup, a starch paste, gum arabic, a cellulose solution or a polymer solution, stirred to mix, dried and pulverized to provide granules. Instead of granulating, the powder may be compression-molded with a tablet machine and the resulting slugs, i.e. an incomplete product, be crushed to provide granules. The granules thus obtained can be protected against inter-adhesion or caking by adding a lubricant such as stearic acid, its salt, talc, mineral oil or the like. The thus-lubricated mixture can then be compressed into tablets. The bare tablets so obtained can be film-coated or sugar-coated. The drug of the invention may optionally be directly compressed into tables after admixing it with a free-flowing inert carrier, omitting said granulation or slugging operation. A transparent or translucent protective coat such as a hermetic shellac coat and a wax glaze coat may also be applied.

Other products for oral administration, such as a solution, a syrup, a troche, an elixir, etc., can also be provided in unit dose forms each containing a calculated amount of the drug of the invention. The syrup can be manufactured by dissolving the drug of the invention in a suitable flavored aqueous medium and the elixir can be manufactured using a nontoxic alcoholic vehicle. The suspension can be manufactured by dispersing the drug of the invention in a nontoxic vehicle. Where necessary, a solubilizer and/or an emulsifier (e.g. ethoxylated isostearyl alcohols, polyoxyethylene-sorbitol esters, etc.), a preservative and a flavoring agent or corrident (e.g. peppermint oil, saccharin) can also be added.

Where necessary, the unit dose formulation for oral administration may be microencapsulated. This formulation may be coated with or embedded in a polymer, wax or other matrix for prolonging the drug action or ensuring a sustained release of the drug.

The composition for non-oral administration can be provided in liquid dosage forms for subcutaneous, intramuscular or intravenous administration, such as a solution or a suspension. Those dosage forms can be manufactured by suspending or dissolving a calculated amount of the drug of the invention in a nontoxic liquid vehicle for injection, such as an aqueous or oily medium, and sterilizing the resulting solution or suspension. To render such an injection isotonic, a nontoxic salt or its solution can be added. Moreover, a stabilizer, a preservative, an emulsifier, etc. can also be added.

The suppositories can be manufactured by dissolving or suspending the compound in a water-soluble or insoluble low-melting solid base such as polyethylene glycol, cacao butter, semi-synthetic oil (e.g. Witepsol® ), a higher ester (e.g. myristyl palmitate) or a mixture thereof.

EXAMPLES

The following test example illustrates the usefulness of the drug of the invention in the treatment of urinary frequency or urinary incontinence and describes this invention in further detail.

Test Example

Cystometry test: Effect on the lower urinary tract function

Female Sprague-Dawley rats weighing 180–230 g (SLC Japan) were respectively immobilized in supine position under urethane anesthesia (900 mg/kg s.c.). After a midline incision was made in the lower abdominal region, the ureters were ligated and cut on the bladder side. The urine from the kidneys was withdrawn from the body through cannulae inserted into the ureters. A T-tube was connected to the free end of a cannula inserted into the bladder apex. Then, warmed saline was infused from one branch of the T-tube into the urinary bladder at a rate of 2.8 ml/hr until the reflex micturition had occurred and the change in intravesical pressure during the intervening time was recorded from the other branch. In this cystometry test, the bladder capacity (the capacity of the urinary bladder at reflex micturition) and the maximum bladder contraction pressure (the maximum intravesical pressure at voiding) were confirmed to occur in a steady manner twice consecutively, after which the test drug (tramadol hydrochloride, supplied by Grunenthal GmbH) was administered intraduodenally. After 30, 60, 120 and 180 minutes, cystometry was performed to examine changes in bladder capacity and maximum bladder contraction pressure. During the above experiment, the animal's body temperature was kept constant using a warming device.

The results of the above experiment were expressed as the mean ±S.E of bladder capacity or maximum bladder contraction pressure, and statistical analysis was made between the control and drug-treated groups by one-way analysis of variance, followed by the Dunnett multiple comparison. The level of significance was $p<0.05$. The test drug (tramadol hydrochloride) was dissolved in physiological saline at concentrations appropriate for an injection volume of 1 ml/kg. The control group received the same volume of saline via the duodenum.

The effect on bladder capacity is shown in Table 1 and effect on maximum bladder contraction pressure is shown in Table 2.

TABLE 1

(Bladder capacity)

| Drug | Dose (mg/kg) | N | Before dosing | After 30 min | After 60 min | After 120 min | After 180 min |
|---|---|---|---|---|---|---|---|
| | | | | Bladder capacity (ml) | | | |
| Control | — | 5 | 0.39 ± 0.02 | 0.39 ± 0.02 | 0.39 ± 0.03 | 0.39 ± 0.03 | 0.40 ± 0.03 |
| Test | 0.3 | 5 | 0.37 ± 0.03 | 0.40 ± 0.05 | 0.34 ± 0.04 | 0.35 ± 0.03 | 0.38 ± 0.03 |

TABLE 1-continued (Bladder capacity)

| Drug | Dose (mg/kg) | N | Before dosing | Bladder capacity (ml) | | | |
|------|--------------|---|---------------|-----------------------|---|---|---|
| | | | | After 30 min | After 60 min | After 120 min | After 180 min |
| drug | 1 | 5 | 0.36 ± 0.02 | 0.49 ± 0.05 | 0.49 ± 0.08 | 0.44 ± 0.06 | 0.42 ± 0.03 |
| | 3 | 5 | 0.36 ± 0.01 | 0.62 ± 0.04** | 0.61 ± 0.04** | 0.53 ± 0.07 | 0.50 ± 0.07 |

N represents the number of animals.
Each bladder capacity value represents the mean ± standard error.
**: p < 0.01 (versus control group)

TABLE 2

(Maximum bladder contraction pressure)

| Drug | Dose (mg/kg) | N | Before dosing | Maximum contraction pressure (mmHg) | | | |
|------|--------------|---|---------------|--------------------------------------|---|---|---|
| | | | | After 30 min | After 60 min | After 120 min | After 180 min |
| Control | — | 5 | 20.86 ± 1.26 | 19.95 ± 1.12 | 20.63 ± 0.93 | 20.64 ± 0.58 | 21.41 ± 0.63 |
| Test | 0.3 | 5 | 21.32 ± 2.04 | 22.65 ± 2.07 | 21.67 ± 1.31 | 21.90 ± 1.72 | 20.63 ± 1.74 |
| drug | 1 | 5 | 22.52 ± 1.25 | 22.81 ± 1.93 | 21.94 ± 1.23 | 22.02 ± 1.66 | 20.00 ± 1.58 |
| | 3 | 5 | 21.96 ± 1.18 | 23.96 ± 2.34 | 22.70 ± 2.23 | 21.30 ± 2.48 | 21.27 ± 3.22 |

N represents the number of animals.
Each maximum bladder contraction pressure value represents the mean ± standard error.

It is indicated from Table 1 that the test drug tramadol hydrochloride caused a tendency toward increased bladder capacity at the dose level of 1 mg/kg and a significant increase in bladder capacity at 30 and 60 minutes after dosing at 3 mg/kg. From Table 2, it can be seen that the test drug tramadol hydrochloride had no significant difference from the control in terms of the absence of influencing the maximum bladder contraction pressure, thus suggesting that the drug has only a low risk for increasing residual urine.

EFFECT OF THE INVENTION

As mentioned above, it is apparent that the drug of the invention is available not only for an analgesic drug, but also for the treatment of urinary frequency or urinary incontinence.

What is claimed is:

1. A method of treating or prophylaxis of urinary frequency in a subject comprising administering to the subject a therapeutic or prophylactic composition comprising tramadol or a salt thereof.

2. A method of treating or prophylaxis of urinary incontinence in a subject comprising administering to the subject a therapeutic or prophylactic composition comprising tramadol or a salt thereof.

3. The method of claim 1, wherein the therapeutic or prophylactic composition comprises tramadol hydrochloride.

4. The method of claim 2, wherein the therapeutic or prophylactic composition comprises tramadol hydrochloride.

* * * * *